(12) United States Patent
Imamura et al.

(10) Patent No.: US 6,338,782 B1
(45) Date of Patent: Jan. 15, 2002

(54) GAS SENSOR

(75) Inventors: Shinichiro Imamura, Kariya; Tomio Sugiyama, Nagoya; Akio Tanaka, Gifu, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/432,766

(22) Filed: Nov. 3, 1999

(30) Foreign Application Priority Data

Nov. 4, 1998 (JP) ............................................. 10-313385

(51) Int. Cl.[7] ............................................. G01N 27/407
(52) U.S. Cl. ........................ 204/424; 204/426; 204/427; 219/541; 219/548
(58) Field of Search ................................ 204/424, 425, 204/426, 427, 428, 429; 219/541, 543, 546, 548; 338/322, 327

(56) References Cited

U.S. PATENT DOCUMENTS

| | | | |
|---|---|---|---|
| 5,556,526 A | * 9/1996 | Fukaya et al. | 204/425 |
| 5,672,811 A | 9/1997 | Kato et al. | 71/31.05 |
| 5,695,625 A | * 12/1997 | Yamada et al. | 204/427 |
| 4,909,922 A | * 2/1999 | Kato et al. | 204/406 |
| 5,866,799 A | * 2/1999 | Kato et al. | 204/425 |

FOREIGN PATENT DOCUMENTS

| | | |
|---|---|---|
| JP | 8-271476 | 10/1996 |
| JP | 11-23516 | 1/1999 |

* cited by examiner

*Primary Examiner*—Robert J. Warden, Sr.
*Assistant Examiner*—Kaj K. Olsen
(74) *Attorney, Agent, or Firm*—Pillsbury Winthrop LLP

(57) ABSTRACT

A gas sensor includes a body having a measurement-gas chamber and a reference-gas chamber. The measurement-gas chamber is supplied with a measurement gas. The reference-gas chamber is supplied with a reference gas. A detecting cell provided in the body includes (1) a solid electrolyte member, (2) a measuring electrode provided on the solid electrolyte member and facing the measurement-gas chamber, and (3) a reference electrode provided on the solid electrolyte member and facing the reference-gas chamber. A heater portion operates for heating the detecting cell. The heater portion includes (1) a first substrate, (2) a heating member provided on the first substrate, (3) a high-voltage-side lead portion provided on the first substrate and electrically connected to the heating member, (4) a low-voltage-side lead portion provided on the first substrate and electrically connected to the heating member, and (5) a second substrate covering the heating member. The first substrate has a first surface and a second surface opposite to each other. The first surface of the first substrate faces the body. The heating member extends on the first surface of the first substrate. The high-voltage-side lead portion extends on the second surface of the first substrate.

8 Claims, 12 Drawing Sheets

GAS SENSOR

BACKGROUND OF THE INVENTION

1. Field of the Invention

This invention relates to a gas sensor for detecting a concentration of a specific component, for example, a NOx component of a measurement gas. An example of the measurement gas is an exhaust gas emitted from an internal combustion engine.

2. Description of the Related Art

In general, a NOx concentration sensor is necessary to implement feedback control of an automotive engine to reduce NOx emission therefrom. A NOx concentration sensor located at a point in an engine exhaust passage downstream of a NOx-processing catalytic converter can be used in a system for determining whether or not the catalytic converter has significantly deteriorated.

A prior-art NOx concentration sensor has characteristics which tend to be affected by a temperature change.

SUMMARY OF THE INVENTION

It is an object of this invention to provide an improved gas sensor.

A first aspect of this invention provides a gas sensor comprising a body having a measurement-gas chamber and a reference-gas chamber, the measurement-gas chamber being supplied with a measurement gas, the reference-gas chamber being supplied with a reference gas; a detecting cell provided in the body and including (1) a solid electrolyte member, (2) a measuring electrode provided on the solid electrolyte member and facing the measurement-gas chamber, and (3) a reference electrode provided on the solid electrolyte member and facing the reference-gas chamber; and a heater portion for heating the detecting cell, the heater portion including (1) a substrate, (2) a heating member provided on the substrate, and (3) a high-voltage-side lead portion provided on the substrate and electrically connected to the heating member; wherein the substrate has a first surface and a second surface opposite to each other, and the first surface of the substrate faces the body, and wherein the heating member extends on the first surface of the substrate, and approximately the entire length of the high-voltage-side lead portion extends on the second surface of the substrate.

A second aspect of this invention is based on the first aspect thereof, and provides a gas sensor wherein the heater portion further includes a low-voltage-side lead portion provided on the substrate and electrically connected to the heating member, the low-voltage-side lead portion extending on the first surface of the substrate.

A third aspect of this invention is based on the second aspect thereof, and provides a gas sensor wherein the heater portion further includes an insulating member provided on the substrate and having an opening of a negative pattern with respect to the heating member and the low-voltage-side lead portion, and wherein the heating member and the low-voltage-side lead portion fit in the opening in the insulating member.

A fourth aspect of this invention provides a gas sensor comprising a body having a measurement-gas chamber and a reference-gas chamber, the measurement-gas chamber being supplied with a measurement gas, the reference-gas chamber being supplied with a reference gas; a detecting cell provided in the body and including (1) a solid electrolyte member, (2) a measuring electrode provided on the solid electrolyte member and facing the measurement-gas chamber, and (3) a reference electrode provided on the solid electrolyte member and facing the reference-gas chamber; and a heater portion for heating the detecting cell, the heater portion including (1) a first substrate, (2) a heating member provided on the first substrate, (3) a high-voltage-side lead portion provided on the first substrate and electrically connected to the heating member, (4) a low-voltage-side lead portion provided on the first substrate and electrically connected to the heating member, and (5) a second substrate covering the heating member; wherein the first substrate has a first surface and a second surface opposite to each other, and the first surface of the first substrate faces the body, and wherein the heating member extends on the first surface of the first substrate, and the high-voltage-side lead portion extends on the second surface of the first substrate.

DESCRIPTION OF THE PREFERRED EMBODIMENTS

A prior-art NOx concentration sensor will be explained for a better understanding of this invention.

Figure 1:
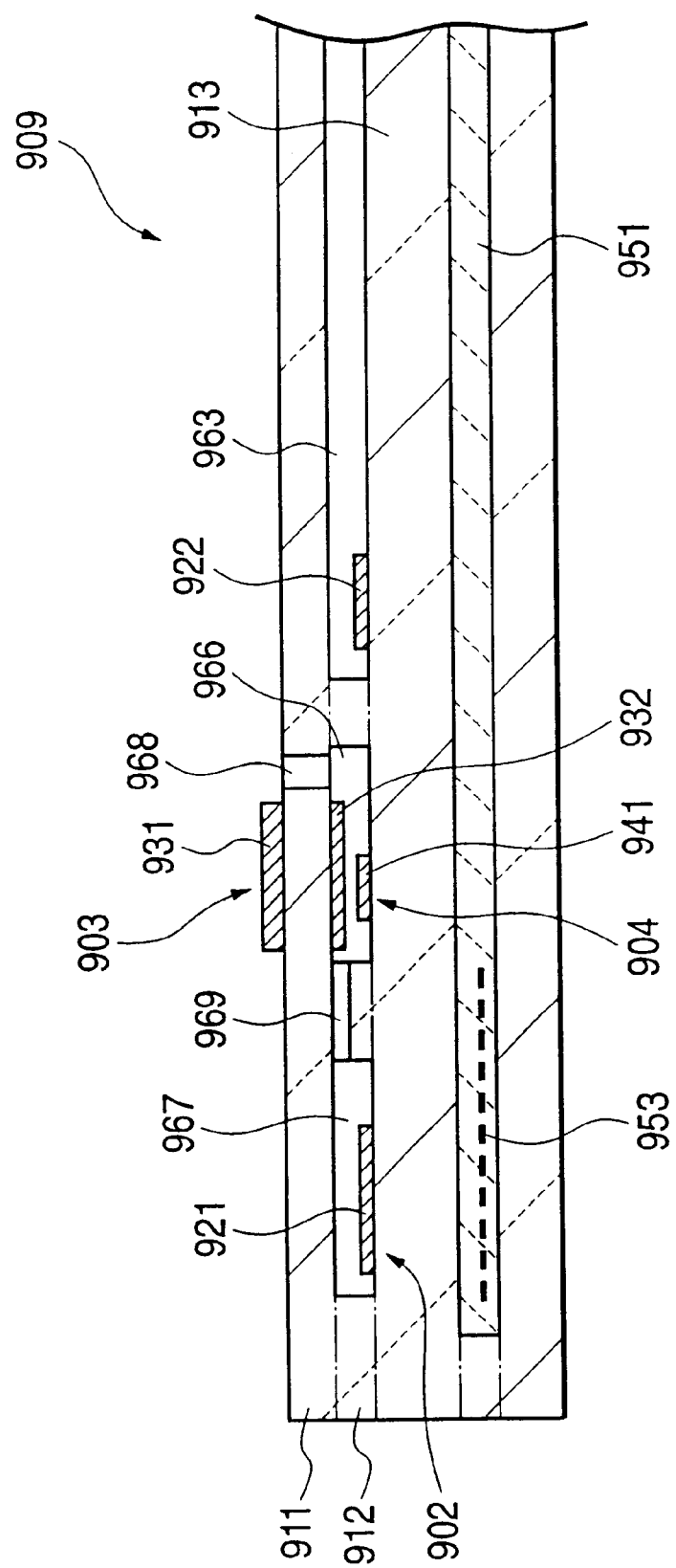
FIG. 1 is a sectional diagram of a prior-art NOx concentration sensor.

FIG. 1 shows a prior-art NOx concentration sensor 909 disclosed in U.S. Pat. No. 5,672,811 which corresponds to Japanese published unexamined patent application 8-271476.

With reference to FIG. 1, the prior-art sensor 909 has a first internal space 966 and a second internal space 967. A measurement gas is introduced into the first internal space 966 via a first diffusion controlling passage 968. The measurement gas is introduced into the second internal space 967 from the first internal space 966 via a second diffusion controlling passage 969. Also, the prior-art sensor 909 has a chamber 963 supplied with a reference gas.

The prior-art sensor 909 includes a first electrochemical pumping cell 903 for controlling the oxygen-gas concentration in the measurement gas within the first internal space 966. The first electrochemical pumping cell 903 is composed of electrodes 931 and 932, and a solid electrolyte layer 911 extending between the electrodes 931 and 932. The electrode 931 is exposed at an exterior of the sensor 909 while the electrode 932 faces the first internal space 966. In addition, the prior-art sensor 909 includes an electrochemical sensing cell 904 for detecting the oxygen-gas concentration in the measurement gas within the first internal space 966. The electrochemical sensing cell 904 is composed of a reference electrode 922, a measuring electrode 941, and a solid electrolyte layer 913 on which the electrodes 922 and 941 are formed. The reference electrode 922 faces the reference-gas chamber 963 while the measuring electrode 941 faces the first internal space 966. Furthermore, the prior-art sensor 909 includes a second electrochemical pumping cell 902 for detecting the NOx-gas concentration in the measurement gas within the second internal space 967. The second electrochemical pumping cell 902 is composed of a pumping electrode 921, the reference electrode 922, and the solid electrolyte layer 913. The pumping electrode 921 is formed on the solid electrolyte layer 913. The pumping electrode 921 faces the second internal space 967.

A series combination of an ammeter and a dc power supply is electrically connected between the pumping electrode 921 and the reference electrode 922. The current which is measured by the ammeter indicates the NOx-gas concentration in the measurement gas.

The prior-art sensor 909 incorporates an alumina insulating layer 951 laminated integrally on the side of the solid electrolyte layer 913 which is remoter from the first internal space 966, the second internal space 967, and the reference chamber 963. A heater 953 is embedded within the alumina insulating layer 951. The heater 953 extends directly below the second internal space 967 so that the second internal space 967 can be heated to a higher temperature than that of the first internal space 966. The heater 953 enables the second electrochemical pumping cell 902 to perform its desired function more effectively.

A drive current to the heater 953 tends to more leak into the solid electrolyte layer 913 as the temperature of the prior-art sensor 909 rises. Such a leak current causes an error in the measured value of the NOx-gas concentration which is obtained via the ammeter. Since the magnitude of the leak current depends on the temperature, the measured NOx-gas concentration provided by the prior-art sensor 909 tends to be adversely affected by a temperature change.

First Embodiment

Figure 2:
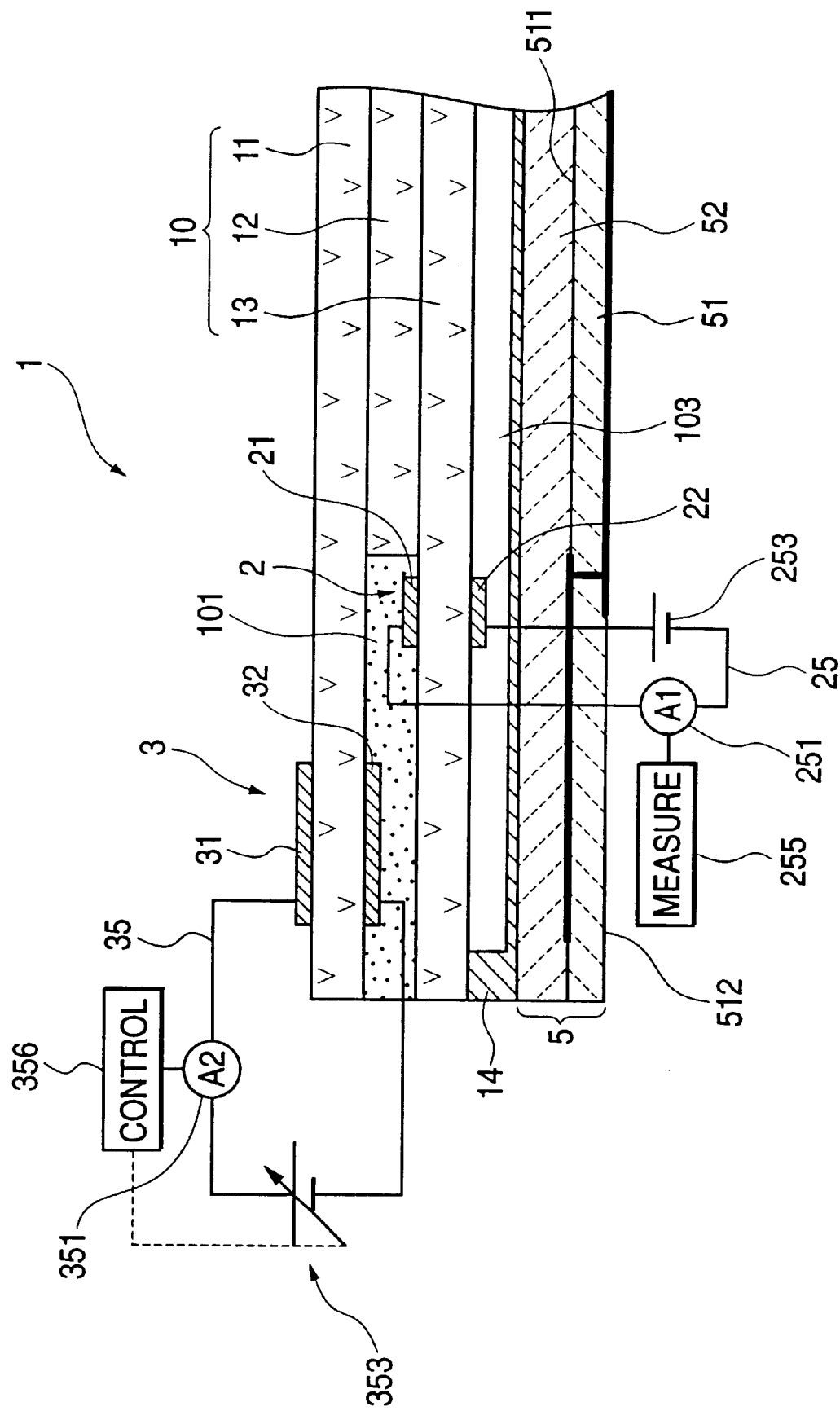
FIG. 2 is a sectional diagram of a gas sensor according to a first embodiment of this invention.

FIG. 2 shows a gas sensor 1 according to a first embodiment of this invention. As shown in FIG. 2, the gas sensor 1 has a chamber 101 into which a measurement gas is introduced. The measurement-gas chamber 101 is filled with porous material. Also, the gas sensor 1 has a chamber 103 into which a reference gas is introduced.

The gas sensor 1 includes a detecting cell 2 and a pumping cell 3. The detecting cell 2 has a measuring electrode 21, a reference electrode 22, and a solid electrolyte layer 13. The measuring electrode 21 and the reference electrode 22 are formed on the opposite surfaces of the solid electrolyte layer 13, respectively. The measuring electrode 21 and the reference electrode 22 are parallel and align with each other. The measuring electrode 21 faces the measurement-gas chamber 101. The reference electrode 22 faces the reference-gas chamber 103. A lower portion of the gas sensor 1 is formed by a heater portion 5. The heater portion 5 acts to heat the detecting cell 2.

A body 10 of the gas sensor 1 includes a laminate of solid electrolyte layers 11 and 12. The solid electrolyte layer 11 extends on the solid electrolyte layer 12. The sensor body 10 also includes the solid electrolyte layer 13. The solid electrolyte layer 12 extends on the solid electrolyte layer 13. Furthermore, the sensor body 10 includes an insulating base or an insulating substrate 14 on which the solid electrolyte layer 13 is formed. The insulating base 14 extends on the heater portion 5.

With reference to FIG. 2, the solid electrolyte layers 11 and 13 extend further than the solid electrolyte layer 12 in the horizontal direction so that a space is defined among the solid electrolyte layers 11, 12, and 13. This space is the measurement-gas chamber 101. The measurement-gas chamber 101 is charged with a porous member for offering a desired diffusion resistance to the measurement gas which is being introduced thereinto.

The pumping cell 3 has the solid electrolyte layer 11, and a pair of pumping electrodes 31 and 32 formed on the opposite sides of the solid electrolyte layer 11 respectively. The pumping electrodes 31 and 32 are parallel and align with each other. The pumping electrode 31 is exposed at an exterior of the gas sensor 1. The pumping electrode 32 faces the measurement-gas chamber 101. The location of the pumping cell 3 relative to an inlet of the measurement-gas chamber 101 is shallower than that of the detecting cell 2. In other words, the pumping cell 3 is positionally upstream of the detecting cell 2 with respect to the flow of the measurement gas in the measurement-gas chamber 101.

With reference to FIG. 2, an upper surface of the insulating base 14 has a groove or a recess which forms the reference-gas chamber 103. The reference-gas chamber 103 is defined between the solid electrolyte layer 13 and the insulating base 14.

The measuring electrode 21 of the detecting cell 2 is made of platinum (Pt) or a noble metal alloy which has a high catalytic activity. Thus, the measuring electrode 21 acts on the surrounding measurement gas in the measurement-gas chamber 101. Specifically, the measuring electrode 21 has the function of decomposing NOx in the surrounding measurement gas into nitrogen and oxygen through reaction as "$NOx \rightarrow (1/2)N_2 + (x/2)O_2$". The detecting cell 2 pumps oxygen ($O_2$) from the measurement-gas chamber 101 to the reference-gas chamber 103 when being fed with electric power. The reference electrode 22 of the detecting cell 2 is also made of platinum (Pt). Alternatively, the reference electrode 22 may be made of a gold-platinum alloy (Au—Pt).

The electrode 31 of the pumping cell 3 is made of platinum (Pt). The electrode 32 of the pumping cell 3 is made of a gold-platinum alloy (Au—Pt) which is inactive to NOx, that is, which does not decompose NOx. The pumping cell 3 transfers oxygen ($O_2$) from the measurement-gas chamber 101 to the external space around the gas sensor 1 or from the external space to the measurement-gas chamber 101 when being fed with electric power.

Figure 3:
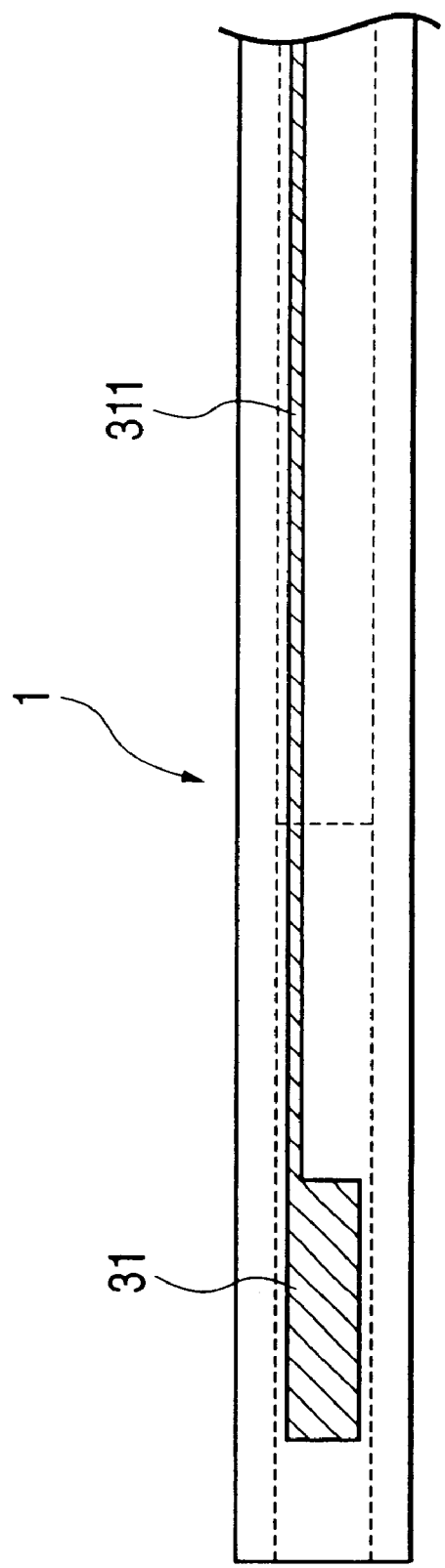
FIG. 3 is a plan view of the gas sensor in FIG. 2.
Figure 4:
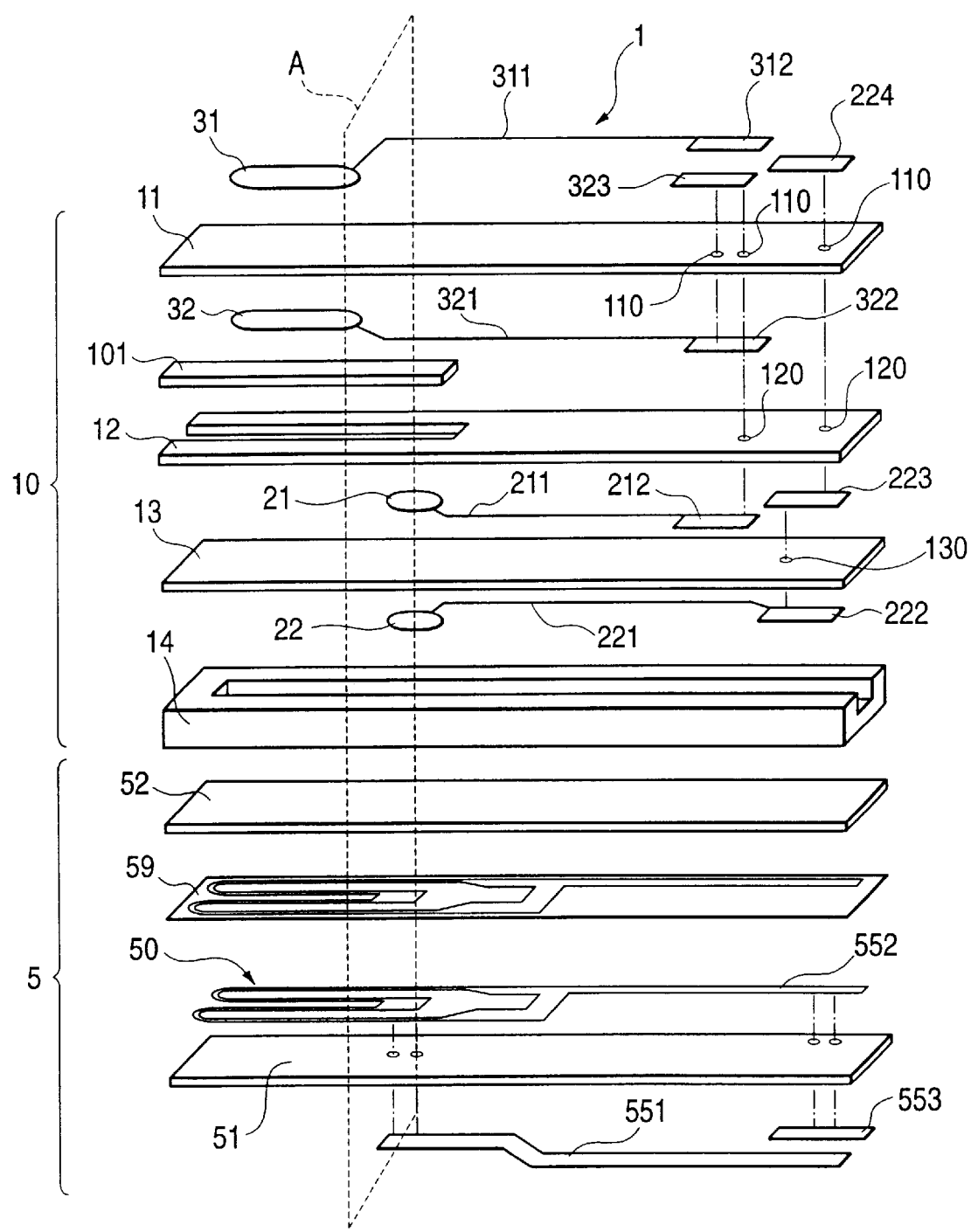
FIG. 4 is an exploded view of the gas sensor in FIG. 2.

As shown in FIGS. 3 and 4, a lead portion 311 extends between a terminal 312 and the electrode 31 of the pumping cell 3. The lead portion 311 electrically connects the terminal 312 and the pumping electrode 31. As shown in FIG. 4, a lead portion 321 extends between a terminal 322 and the electrode 32 of the pumping cell 3. The lead portion 321 electrically connects the terminal 322 and the pumping electrode 32. The terminal 322 is electrically connected to a terminal 323 via a through hole 110 in the solid electrolyte layer 11.

As shown in FIG. 4, a lead portion 211 extends between a terminal 212 and the measuring electrode 21 of the detecting cell 2. The lead portion 211 electrically connects the terminal 212 and the measuring electrode 21. The terminal 212 is electrically connected to the terminal 323 via a through hole 120 in the solid electrolyte layer 12 and a through hole 110 in the solid electrolyte layer 11. A lead portion 221 extends between a terminal 222 and the reference electrode 22 of the detecting cell 2. The lead portion 221 electrically connects the terminal 222 and the reference electrode 22. The terminal 222 is electrically connected to a terminal 223 via a through hole 130 in the solid electrolyte layer 13. The terminal 223 is electrically connected to a terminal 224 via a through hole 120 in the solid electrolyte layer 12 and a through hole 110 in the solid electrolyte layer 11. Thus, the terminal 222 is electrically connected to the terminal 224.

The heater portion 5, the insulating base 14, and the solid electrolyte layer 13 are arranged in a laminate in that order. As previously mentioned, the upper surface of the insulating base 14 has the groove which forms the reference-gas chamber 103. The reference-gas chamber 103 is defined between the solid electrolyte layer 13 and the insulating base 14.

Figure 5:
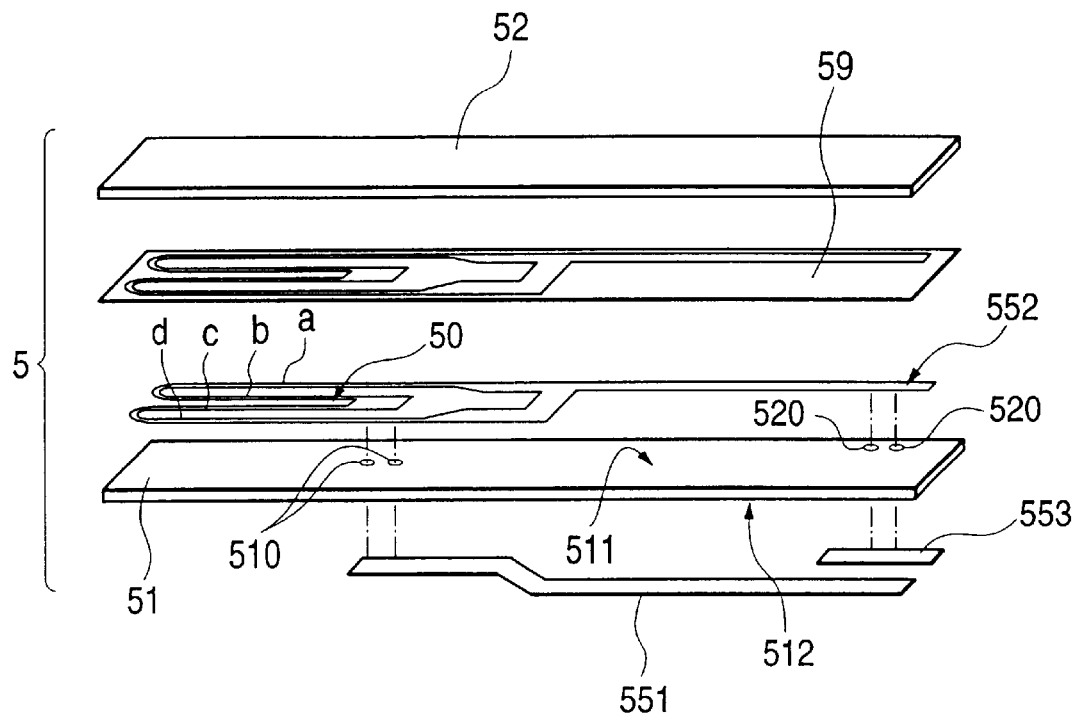
FIG. 5 is an exploded view of a heater portion in the gas sensor of FIG. 2.

As shown in FIG. 5, the heater portion 5 includes a heating member 50, a heater substrate 51, and a cover substrate 52. The heater substrate 51 is made of insulating material. Also, the cover substrate 52 is made of insulating material. The heating member 50 contains platinum (Pt). The heating member 50 is provided on the upper surface 511 of the heater substrate 51 which is closer to the sensor body 10. A high-voltage-side lead portion 551 is provided on the lower surface 512 of the heater substrate 51 which is remoter from the sensor body 10. An end of the high-voltage-side lead portion 551 is electrically connected to the heating member 50 via through holes 510 in the heater substrate 51. A low-voltage-side lead portion 552 extends from the heating member 50. The low-voltage-side lead portion 552 is integral with the heating member 50. The low-voltage-side lead portion 552 is provided on the upper surface 511 of the heater substrate 51. An end of the low-voltage-side lead portion 552 is electrically connected to a terminal 553 via through holes 520 in the heater substrate 51. The terminal 553 is provided on the lower surface 512 of the heater substrate 51. An alumina film 59 having a negative pattern with respect to the heating member 50 and the low-voltage-side lead portion 552 is provided on the upper surface 511 of the heater substrate 51. Thus, the heating member 50 and the low-voltage-side lead portion 552 fit in an opening through the alumina film 59. The cover substrate 52 is superposed on the heating member 50, the low-voltage-side lead portion 552, and the alumina film 59 to cover them. It should be noted that the high-voltage-side lead portion 551 may be coated with a cover substrate or an insulating layer.

The terminal 553 is electrically connected to the ground terminal or the negative terminal of a heater power supply (not shown) via a conductive wire (not shown). The high-voltage-side lead portion 551 is electrically connected to the positive terminal of the heater power supply via a conductive wire (not shown). Accordingly, a drive current generated by the heater power supply flows successively through the high-voltage-side lead portion 551, the through holes 510, the heating member 50, the low-voltage-side lead portion 552, the through holes 520, and the terminal 553.

Figure 6:
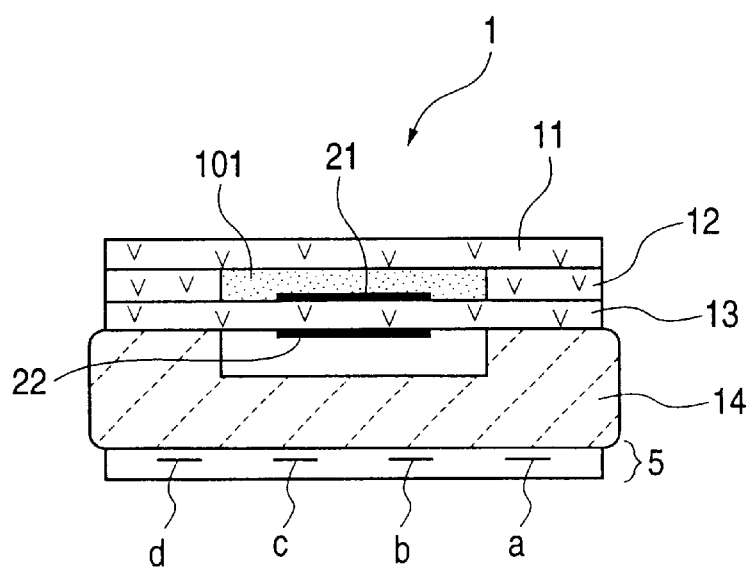
FIG. 6 is a sectional view taken along the plane "A" in FIG. 4.

As shown in FIG. 5, the heating member 50 has portions "a", "b", "c", and "d" parallel with each other. The portions "b" and "c" neighbor each other, and form inner portions respectively. The portion "a" extends outward of the portion "b", and forms an outer portion. The portion "d" extends outward of the portion "c", and forms an outer portion. Regarding an electric path, the portions "b" and "c" are closer to the high-voltage-side lead portion 551 than the portions "a" and "d" are. Thus, potentials (voltages) at the portions "b" and "c" are higher than those at the portions "a" and "d". As best shown in FIG. 6, the heating member 50 is arranged relative to the detecting cell 2 so that the distances between the measuring electrode 21 of the detecting cell 2 and the portions "b" and "c" of the heating member 50 will be shorter than the distances between the measuring electrode 21 and the portions "a" and "d" of the heating member 50. The portions "b" and "c" of the heating member 50 are located at positions directly below the measuring electrode 21.

With reference back to FIG. 2, an electric circuit 25 is connected to the detecting cell 2. The electric circuit 25 includes a current meter 251, a constant-voltage power supply 253, and a measuring device 255. The positive terminal of the power supply 253 is electrically connected to the reference electrode 22 of the detecting cell 2. The negative terminal of the power supply 253 is electrically connected via the current meter 251 to the measuring electrode 21 of the detecting cell 2. The measuring device 255 is connected to the current meter 251. The measuring device 255 calculates a NOx-gas concentration from the detected current value provided by the current meter 251.

An electric (circuit 35 is connected to the pumping cell 3. The electric circuit 35 Includes a current meter 351, a variable-voltage power supply 353, and a controller 356. The positive terminal of the power supply 353 is electrically connected via the current meter 351 lo the electrode 31 of the pumping cell 3. The negative terminal of the power supply 353 is electrically connected to the electrode 32 of the pumping cell 3. The controller 356 is connected between the current meter 351 and the power supply 353. The controller 356 adjusts the output voltage of the power supply 353 in response to the detected current value provided by the current meter 351.

An example of operation of the gas sensor 1 in FIG. 2 is as follows. The gas sensor 1 is connected to an engine exhaust pipe so that an upper surface, a lower surface, and a left-hand surface thereof will be exposed to an exhaust gas emitted from combustion chambers of an internal combustion engine. In this case, the exhaust gas is a measurement gas. An atmosphere is introduced into the reference-gas chamber 103 from an external as a reference gas.

With reference to FIG. 2, the exhaust gas enters the measurement-gas chamber 101 via the left-hand end thereof. In general, the exhaust gas contains gas components such as oxygen ($O_2$), nitrogen oxides (NOx), carbon dioxide ($CO_2$), and water ($H_2O$). The exhaust gas flows rightward in the measurement-gas chamber 101. The voltage generated by the power supply 353 is applied to the pumping cell 3. The voltage application activates the pumping cell 3. A specific component of the exhaust gas is pumped out by the voltage application to the pumping cell 3.

As previously mentioned, the electrode 32 of the pumping cell 3 which faces the measurement-gas chamber 101 is inactive to NOx. Therefore, only oxygen ($O_2$) is pumped from the exhaust gas in the measurement-gas chamber 101. The oxygen ($O_2$) is drawn into the pumping cell 3 from the measurement-gas chamber 101, being transferred through the pumping cell 3 before being discharged via the pumping electrode 31 into the exhaust gas in the external space, that is, the exhaust gas surrounding the main body of the gas sensor 1.

The pumping cell 3 separates only a portion of the oxygen ($O_2$) component from the exhaust gas in the measurement-gas chamber 101. Therefore, the exhaust gas which contains a remaining portion of the oxygen ($O_2$) component flows from the region near the pumping cell 3 to a region in the measurement-gas chamber 101 near the detecting cell 2. The voltage generated by the power supply 253 is applied to the detecting cell 2. The voltage application activates the detecting cell 2. The measuring electrode 21 of the detecting cell 2 decomposes NOx in the surrounding exhaust gas within the measurement-gas chamber 101 through a reaction as "NOx→(1/2)$N_2$+ (x/2)$O_2$". Thus, the decomposition of NOx causes new oxygen ($O_2$). The remaining oxygen ($O_2$) and the new oxygen ($O_2$) are drawn into the detecting cell 2 from the measurement-gas chamber 101, being transferred through the detecting cell 2 before being discharged via the reference electrode 22 into the atmosphere in the reference-gas chamber 103. At this time, an electric current which flows through the detecting cell 2 is detected by the current meter 251 as an indication of a NOx-gas concentration in the exhaust gas. The remaining oxygen ($O_2$) causes a decomposition current which is an offset current superimposed on the NOx-concentration-indicating electric current flowing through the detecting cell 2. The current meter 251 informs the measuring device 255 of the detected current value. The measuring device 255 calculates the NOx-gas concentration in the exhaust gas from the detected current value.

A method of fabricating the gas sensor 1 will be explained below. Green zirconia sheets for the solid electrolyte layers 11, 12, 13 were made as follows. A ceramic-based mixture was prepared. The ceramic-based mixture consisted of 100 parts of yttria partially stabilized zirconia, 1 part of α-alumina, 5 parts of PVB (polyvinyl butyral), 10 parts of DBP (dibutyl phthalate), 10 parts of ethanol, and 10 parts of toluene. Here, "part" and "parts" mean "part by weight" and "parts by weight", respectively. The yttria partially stabilized zirconia contained 6-mol % yttria and 94-mol % zirconia, and had a mean grain diameter of 0.5 μm.

The components of the ceramic-based mixture were blended in a ball mill so that the ceramic-based mixture was made into a slurry. The slurry was dried in a doctor blade method, and was shaped into a ceramic-based sheet having a thickness of 0.3 mm. Three ceramic-based sheets equal to the previously-mentioned ceramic-based sheet were made.

First one of the ceramic-based sheets was cut into a rectangular sheet having a size of 5 mm by 70 mm. Au-added Pt paste was prepared. The Au-added Pt paste contained 1-weight % to 10-weight % gold. A layer of the Au-added Pt paste for the electrode 32 of the pumping cell 3 was formed on the rectangular sheet by a printing process. Pt paste was prepared. Layers and lines of the Pt paste for the electrode 31 of the pumping cell 3, the lead portions 311 and 321, and the terminals 224, 312, 322, and 323 were formed on the rectangular sheet by a screen printing process. The resultant rectangular sheet was a green sheet for the solid electrolyte layer 11.

Second one of the ceramic-based sheets was cut into a rectangular sheet having a size of 5 mm by 70 mm. One end of the rectangular sheet was made into a U-shape having a rectangular opening for the measurement-gas chamber 101. The opening had a size of 2 mm by 15 mm. The resultant rectangular sheet was a green sheet for the solid electrolyte layer 12.

Third one of the ceramic-based sheets was cut into a rectangular sheet having a size of 5 mm by 70 mm. Pd-added Pt paste was prepared. The Pd-added Pt paste contained 0-weight % to 10-weight % palladium. A layer of the Pd-added Pt paste for the measuring electrode 21 of the detecting cell 2 was formed on the rectangular sheet by a printing process. Pt paste was prepared. Layers and lines of the Pt paste for the reference electrode 22 of the detecting cell 2, the lead portions 211 and 221, and the terminals 212, 222, and 223 were formed on the rectangular sheet by a screen printing process. The resultant rectangular sheet was a green sheet for the solid electrolyte layer 13.

Green alumina sheets for the insulating base 14, the heater substrate 51, and the cover substrate 52 were made as follows. A ceramic-based mixture was prepared. The ceramic-based mixture consisted of 98 parts of α-alumina, 3 parts of yttria partially stabilized zirconia, 10 parts of PVB (polyvinyl butyral), 10 parts of DBP (dibutyl phthalate), 30 parts of ethanol, and 30 parts of toluene. Here, "parts" means "parts by weight". The α-alumina had a mean grain diameter of 0.3 μm. The yttria partially stabilized zirconia contained 6-mol % yttria and 94-mol % zirconia.

The components of the ceramic-based mixture were blended in a ball mill so that the ceramic-based mixture was made into a slurry. The slurry was dried in a doctor blade method, and was shaped into a ceramic-based sheet having a thickness of 0.3 mm. Three ceramic-based sheets equal to the previously-mentioned ceramic-based sheet were made.

First one of the ceramic-based sheets was cut into a rectangular sheet having a size of 5 mm by 70 mm. A groove for the reference-gas chamber 103 was formed in one major surface of the rectangular sheet. The groove had a two-dimensional size of 2 mm by 65 mm. The groove extended from one end surface of the rectangular sheet to a position near the other end surface thereof. The resultant rectangular sheet was a green sheet for the insulating base 14.

Second one of the ceramic-based sheets was cut into a rectangular sheet having a size of 5 mm by 70 mm. Alumina-added Pt paste was prepared. The alumina-added Pt paste contained 90-weight % platinum and 10-weight % alumina. Layers of the alumina-added Pt paste for the heating member 50, the lead portions 551 and 552, and the terminal 553 were formed on the rectangular sheet by a screen printing process. The resultant rectangular sheet was a green sheet for the heater substrate 51.

Third one of the ceramic-based sheets was cut into a rectangular sheet having a size of 5 mm by 70 mm. The resultant rectangular sheet was a green sheet for the cover substrate 52.

A green sheet for the alumina film 59 was made as follows. The alumina same as that used for the insulating base 14, the heater substrate 51, and the cover substrate 52 was used. Then, 100 parts of alumina powder, 10 parts of PVB (polyvinyl butyral), 5 parts of DBP (dibutyl phthalate), 1 part of Span, and 50 parts of terpineol were combined into a mixture. Here, "part" and "parts" mean "part by weight" and "parts by weight", respectively. The PVB was used as a binder. The DBP was used as a plasticizer. The Span was used as an antifoamer. The terpineol was used as a solvent. The mixture was repetitively passed through a 3-piece roll 20 times, being made into alumina paste. A layer of the alumina paste which had a negative pattern was made in a screen printing method. The layer was dried, and made into a green sheet for the alumina film 59.

A material for the porous member occupying the measurement-gas chamber 101 was made as follows. First, 100 parts of alumina powder, 10 parts of PVB (polyvinyl butyral), 5 parts of DBP (dibutyl phthalate), 1 part of Span, and 50 parts of terpineol were combined Into a mixture. Here, "part" and "parts" mean "part by weight" and "parts by weight", respectively. The PVB was used as a binder. The DBP was used as a plasticizer. The Span was used as an antifoamer. The terpineol was used as a solvent. The mixture was repetitively passed through a 3-piece roll 20 times, being made into alumina paste. The alumina paste was the material for the porous member.

The previously-mentioned green sheets were combined into a laminate as follows. The green sheet for the solid electrolyte layer 12 and the green sheet for the solid electrolyte layer 13 were connected and laminated by a thermo-compression bonding process at a temperature of 80° C. Subsequently, the opening in the green sheet for the solid electrolyte layer 12 was charged with the alumina paste for the porous member. Thereafter, the other green sheets were sequentially connected and laminated by thermocompression bonding processes to complete a laminate. The laminate was fired in the atmosphere at a temperature of 1,500° C. for 1 hour. As a result, the laminate was changed into the gas sensor 1.

A sample "1" of the gas sensor 1 was fabricated. Also, a sample "C1" of a comparative gas sensor 89 was fabricated. The performances of the samples "1" and "C1" were measured, and were compared with each other.

Figure 7:
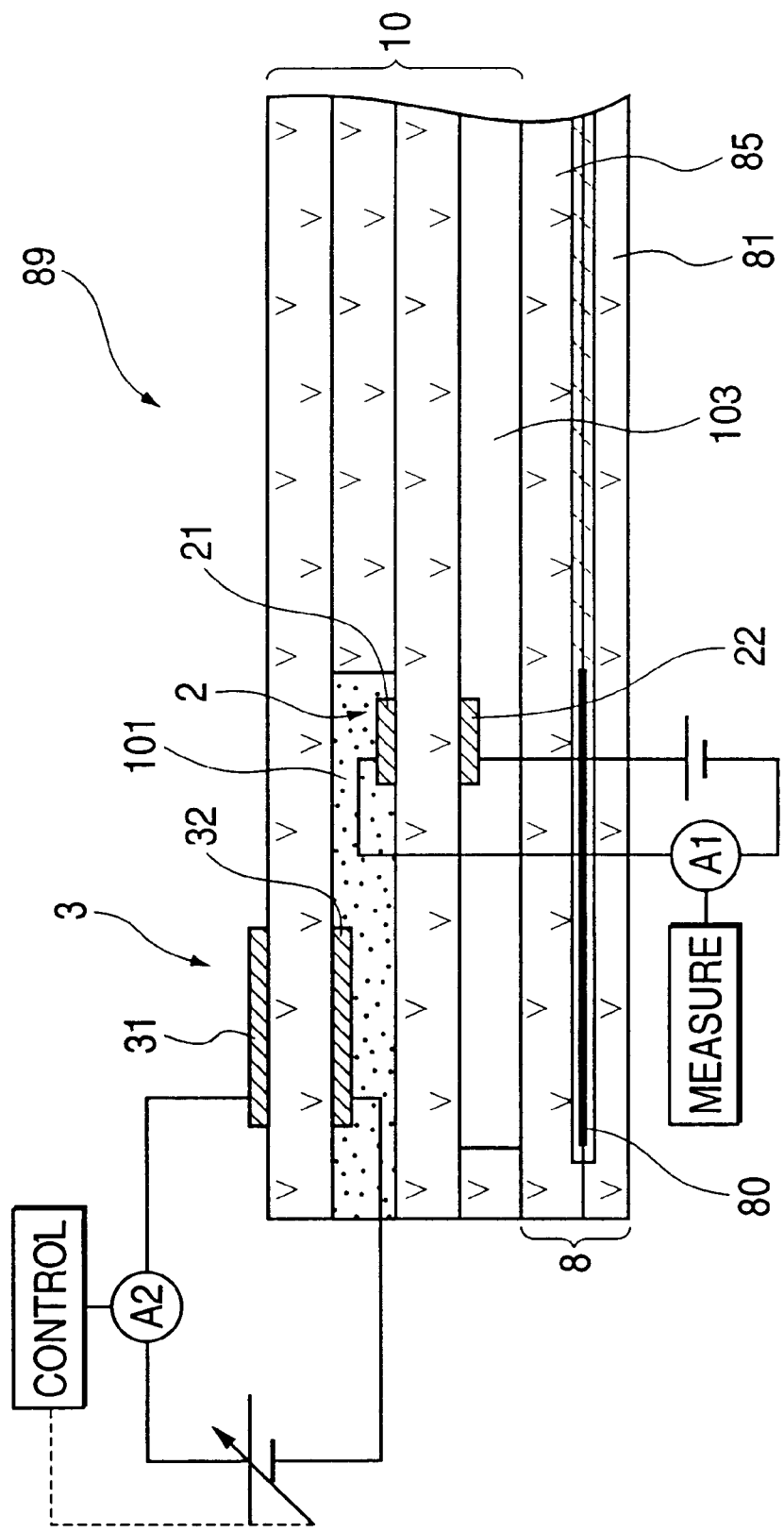
FIG. 7 is a sectional diagram of a comparative gas sensor.
Figure 8:
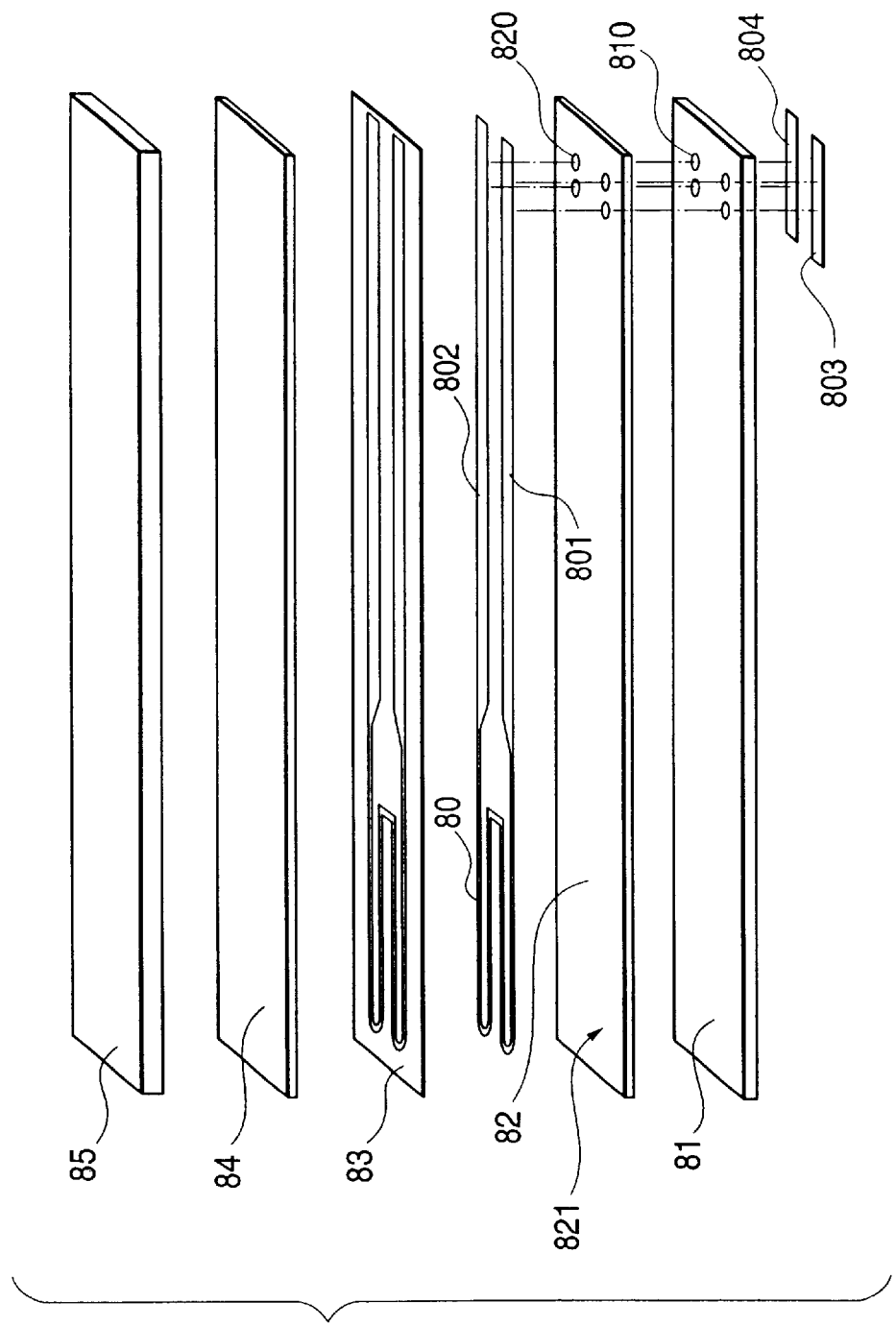
FIG. 8 is an exploded view of a heater portion in the comparative gas sensor of FIG. 7.

FIGS. 7 and 8 show the comparative gas sensor 89. Electrodes 21, 22, 31, and 32 in the comparative gas sensor 89 are the same as those in the gas sensor 1. A measurement-gas chamber 101 and a reference-gas chamber 103 in the comparative gas sensor 89 are the same as those in the gas sensor 1. The comparative gas sensor 89 is basically similar to the gas sensor 1 except for design changes indicated below.

As shown In FIG. 7, the comparative gas sensor 89 includes a heater portion 8 Instead of the heater portion 5 (see FIG. 2). As shown in FIGS. 7 and 8, the heater portion 8 includes a heating member 80, a lower substrate 81, an upper substrate 85, a high-voltage-side lead portion 801, and a low-voltage-side lead portion 802. The high-voltage-side lead portion 801 and the low-voltage-side lead portion 802 extend from the heating member 80. The heating member 80, the high-voltage-side leading portion 801, and the low-voltage-side lead portion 802 are located between the lower substrate 81 and the upper substrate 85.

The lower substrate 81 is made of solid electrolyte. An insulating substrate 82 is superposed on the lower substrate 81. The heating member 80, the high-voltage-side leading portion 801, and the low-voltage-side lead portion 802 are provided on the upper surface 821 of the insulating substrate 82. The high-voltage-side leading portion 801, and the low-voltage-side lead portion 802 are integral with the heating member 80.

Terminals 803 and 804 for electrical connection with a heater power supply (not shown) are provided on the lower surface of the lower substrate 81. The terminals 803 and 804 are electrically connected to the high-voltage-side leading portion 801 and the low-voltage-side lead portion 802 respectively via through holes 810 in the lower substrate 81 and through holes 820 in the insulating substrate 82.

An alumina film 83 having a negative pattern with respect to the heating member 80, the high-voltage-side leading portion 801, and the low-voltage-side lead portion 802 is provided on the upper surface 821 of the insulating substrate 82. Thus, the heating member 80, the high-voltage-side leading portion 801, and the low-voltage-side lead portion 802 fit in an opening through the alumina film 83. An insulating substrate 84 is superposed on the heating member 80, the high-voltage-side leading portion 801, the low-voltage-side lead portion 802, and the alumina film 83 to cover them. The upper substrate 85 is superposed on the insulating substrate 84. The upper substrate 85 is made of solid electrolyte.

The sample "1" of the gas sensor 1 and the sample "C1" of the comparative gas sensor 89 were evaluated regarding characteristics related to NOx and currents leaking from heater portions. The sample "1" of the gas sensor 1 and the sample "C1" of the comparative gas sensor 89 were operated under the conditions where the temperature of measurement gas was 400° C., and the heater portions were activated to maintain the temperatures of the samples at about 750° C. The composition of the measurement gas was as follows. The measurement gas consisted of 0 to 2000-ppm NO, 5% oxygen gas, and nitrogen gas. The NO concentration in the measurement gas was changed. The current value measured by the current meter 251 (see FIG. 2) was recorded. The results of the measurement are shown in FIG. 9.

The sample "1" of the gas sensor 1 and the sample "C1" of the comparative gas sensor 89 were operated under the conditions where the temperature of measurement gas was 400° C., and the heater portions were activated. The temperatures of the samples were changed among 650° C., 700° C., 750° C., and 800° C. The composition of the measurement gas was as follows. The measurement gas consisted of 1000-ppm NO, 5% oxygen gas, and nitrogen gas. The current value measured by the current meter 251 (see FIG. 2) was recorded. The results of the measurement are shown in FIG. 10.

Figure 9:
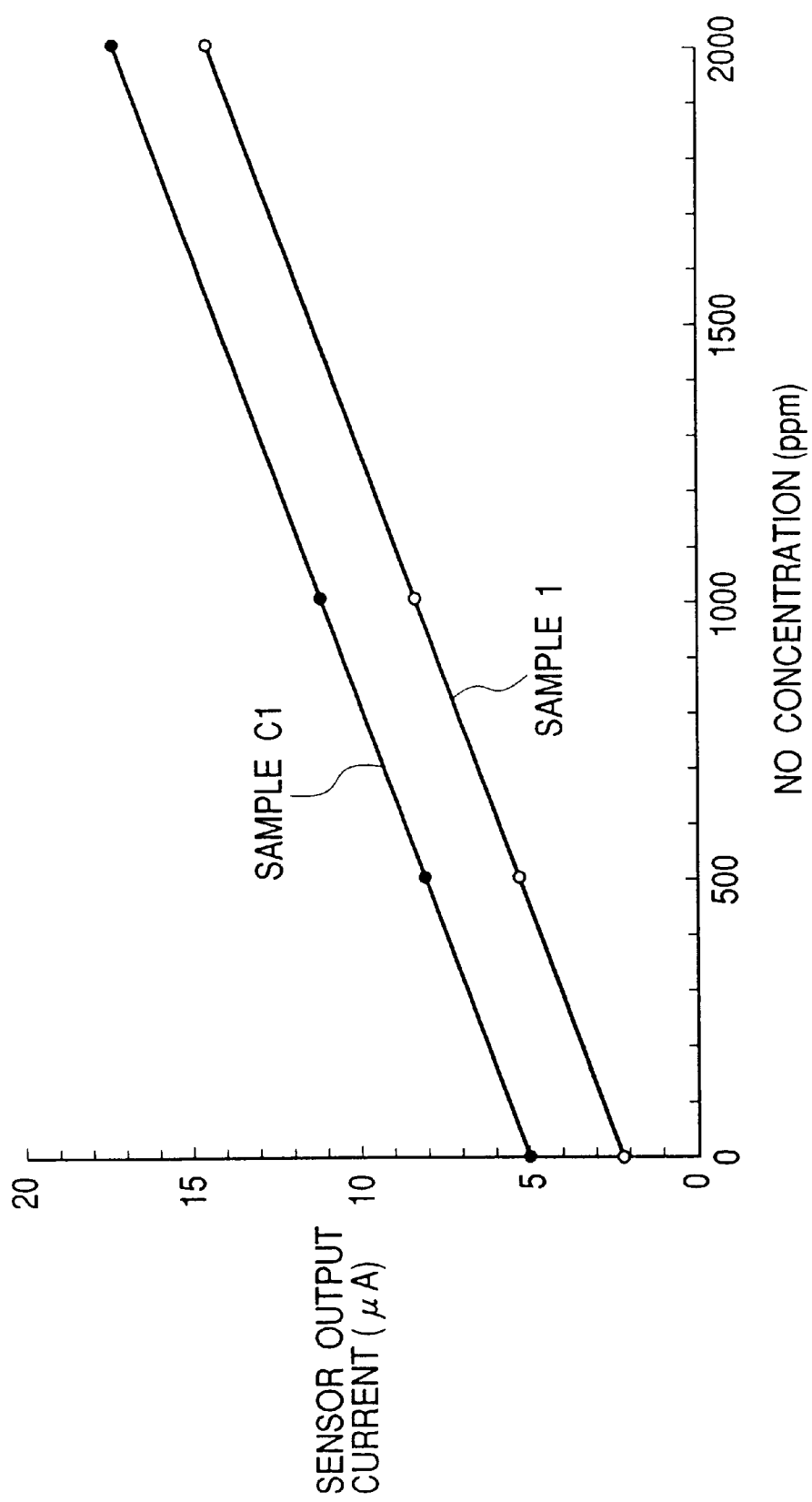
FIG. 9 is a diagram of the experimentally-obtained relation between a sensor output current and a NOx concentration in a measurement gas regarding each of samples of the gas sensor in FIG. 2 and the comparative gas sensor of FIG. 7.

It is shown in FIG. 9 that the sample "1" of the gas sensor 1 is higher than the sample "C1" of the comparative gas sensor 89 in sensor output signal level. It appears that the sample "1" of the gas sensor 1 is less affected by a leak current than the sample "C1" of the comparative gas sensor 89 is.

Figure 10:
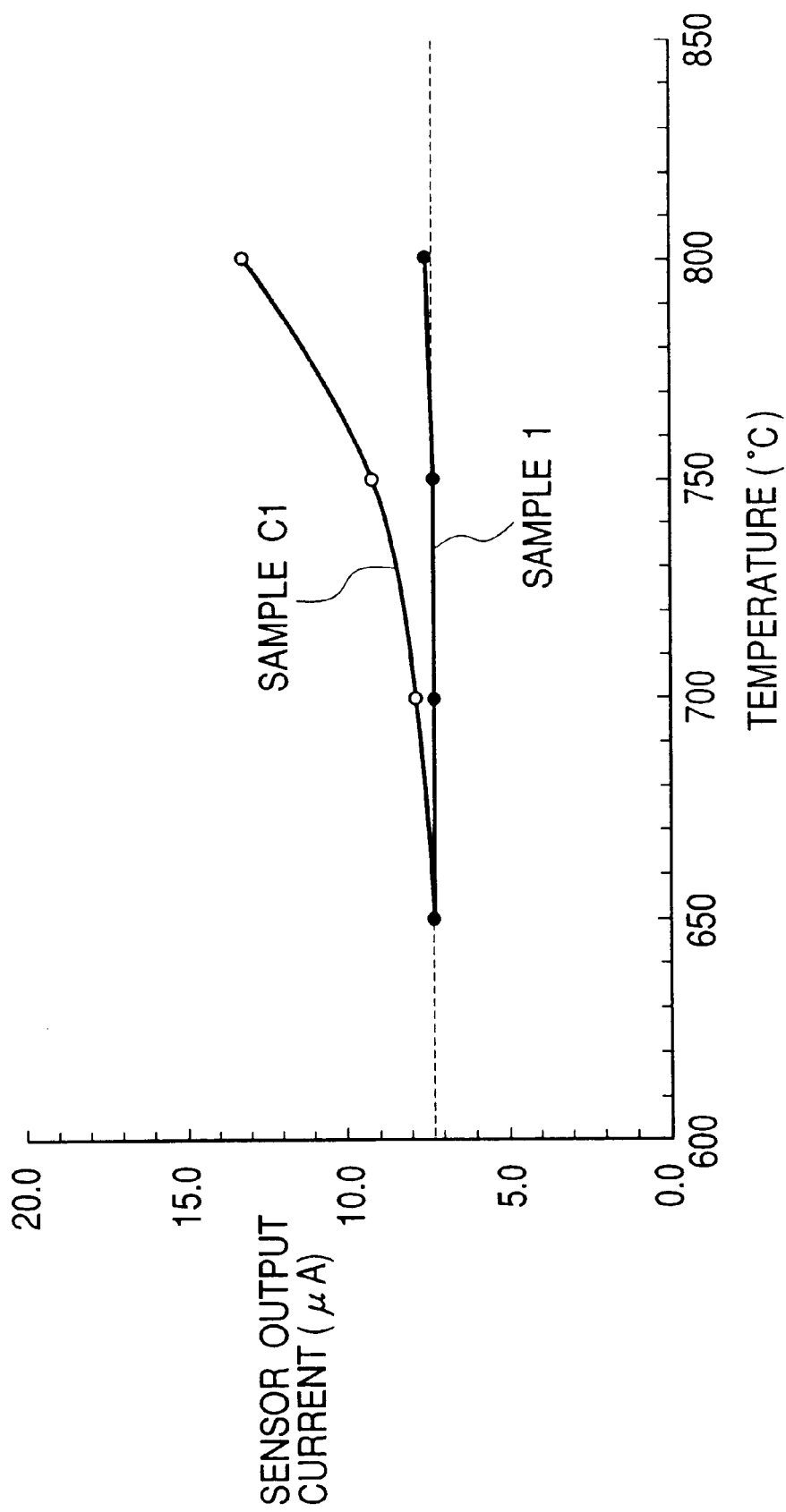
FIG. 10 is a diagram of the experimentally-obtained relation between a sensor output current and a sensor temperature regarding each of the samples of the gas sensor in FIG. 2 and the comparative gas sensor of FIG. 7.

It is shown in FIG. 10 that the output signal from the sample "1" of the gas sensor 1 is less affected by a temperature change than the sample "C1" of the comparative gas sensor 89 is. It is thought that the degree of electric insulation between the heater portion 5 and the sensor body 10 in the sample "1" of the gas sensor 1 is greater than that in the sample "C1" of the comparative gas sensor 89. Thus, it is thought that a current leaking from the heater portion 5 into the sensor body 10 in the sample "1" of the gas sensor 1 is smaller than that in the sample "C1" of the comparative gas sensor 89. It is found that the sample "1" of the gas sensor 1 more accurately detects the NOx-gas concentration in the measurement gas than the sample "C1" of the comparative gas sensor 89 does.

As shown FIGS. 4 and 5, the high-voltage-side lead portion 551 is provided on the lower surface 512 of the heater substrate 51 which is remoter from the sensor body 10 (see FIG. 2) including the detecting cell 2. This arrangement of the high-voltage-side lead portion 551 reduces a leak current therefrom toward the detecting cell 2. As a result of the reduction in the leak current, the gas sensor 1 is substantially independent of a temperature change, and is able to accurately detect the NOx-gas concentration in the measurement gas.

As shown in FIGS. 4 and 5, the heating member 50 is provided on the upper surface 511 of the heater substrate 51 which is closer to the sensor body 10 including the detecting cell 2. Accordingly, the heating member 50 can efficiently heat the detecting cell 2.

Second Embodiment

Figure 11:
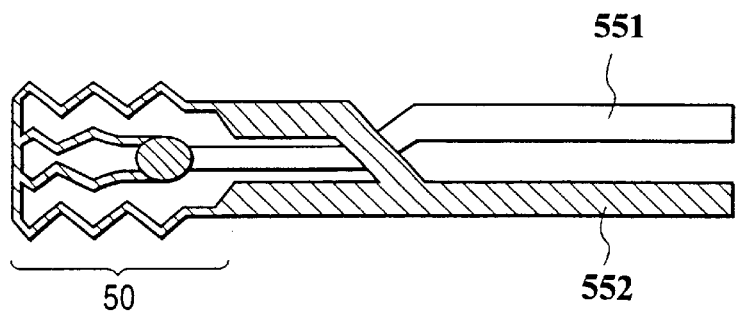
FIG. 11 is a diagram of a heating member, a high-voltage-side lead portion, and a low-voltage-side lead portion in a gas sensor according to a second embodiment of this invention.

A second embodiment of this invention is similar to the first embodiment thereof except for the heating member 50. FIG. 11 shows the heating member 50 in the second embodiment of this invention. The heating member 50 of FIG. 11 includes four zigzag line segments composing portions of the electric path between the high-voltage-side lead portion 551 and the low-voltage-side lead portion 552.

Third Embodiment

Figure 12:
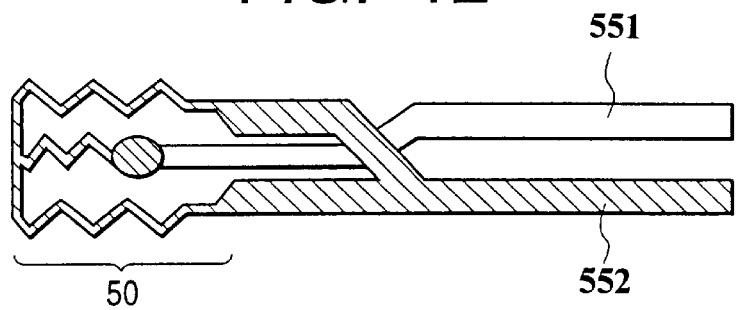
FIG. 12 is a diagram of a heating member, a high-voltage-side lead portion, and a low-voltage-side lead portion in a gas sensor according to a third embodiment of this invention.

A third embodiment of this invention is similar to the first embodiment thereof except for the heating member 50. FIG. 12 shows the heating member 50 in the third embodiment of this invention. The heating member 50 of FIG. 12 includes three zigzag line segments composing portions of the electric path between the high-voltage-side lead portion 551 and the low-voltage-side lead portion 552.

Fourth Embodiment

Figure 13:
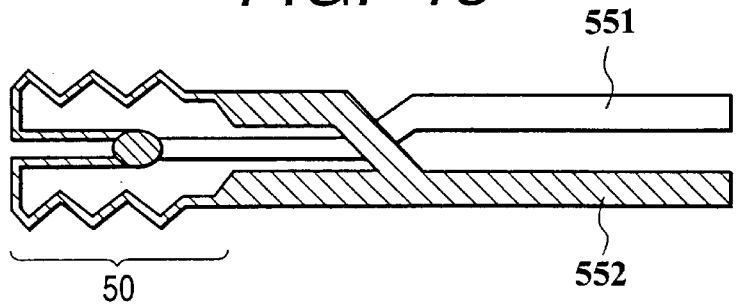
FIG. 13 is a diagram of a heating member, a high-voltage-side lead portion, and a low-voltage-side lead portion in a gas sensor according to a fourth embodiment of this invention.

A fourth embodiment of this invention is similar to the first embodiment thereof except for the heating member 50. FIG. 13 shows the heating member 50 in the fourth embodiment of this invention. The heating member 50 of FIG. 13 includes two zigzag line segments and two straight line segments composing portions of the electric path between the high-voltage-side lead portion 551 and the low-voltage-side lead portion 552.

Fifth Embodiment

Figure 14:
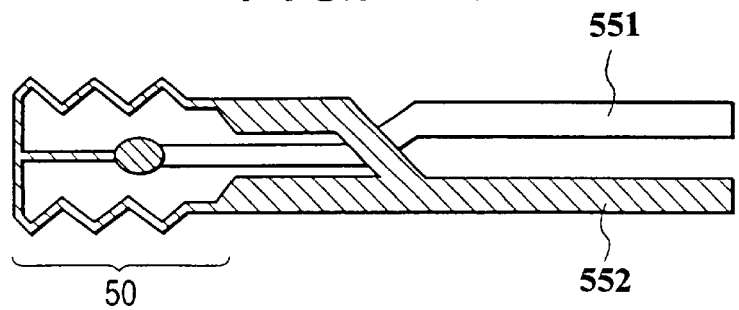
FIG. 14 is a diagram of a heating member, a high-voltage-side lead portion, and a low-voltage-side lead portion in a gas sensor according to a fifth embodiment of this invention.

A fifth embodiment of this invention is similar to the first embodiment thereof except for the heating member 50. FIG. 14 shows the heating member 50 in the fifth embodiment of this invention. The heating member 50 of FIG. 14 includes two zigzag line segments and one straight line segment composing portions of the electric path between the high-voltage-side lead portion 551 and the low-voltage-side lead portion 552.

Sixth Embodiment

Figure 15:
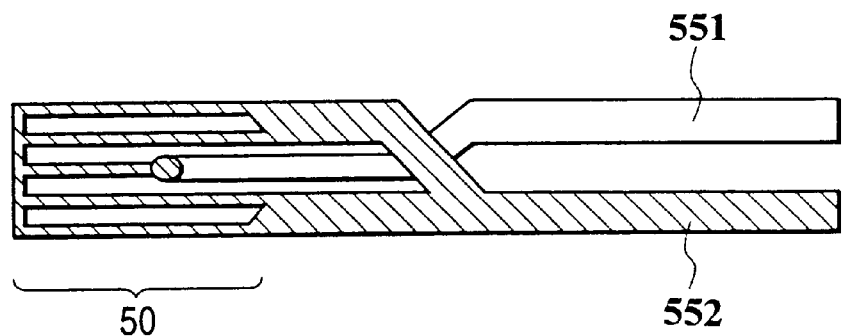
FIG. 15 is a diagram of a heating member, a high-voltage-side lead portion, and a low-voltage-side lead portion in a gas sensor according to a sixth embodiment of this invention.

A sixth embodiment of this invention is similar to the first embodiment thereof except for the heating member 50. FIG. 15 shows the heating member 50 in the sixth embodiment of this invention. The heating member 50 of FIG. 15 includes five straight line segments composing portions of the electric path between the high-voltage-side lead portion 551 and the low-voltage-side lead portion 552.

Seventh Embodiment

Figure 16:
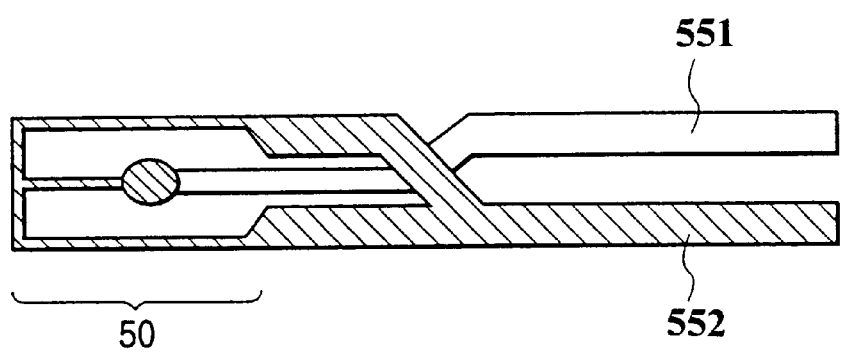
FIG. 16 is a diagram of a heating member, a high-voltage-side lead portion, and a low-voltage-side lead portion in a gas sensor according to a seventh embodiment of this invention.

A seventh embodiment of this invention is similar to the first embodiment thereof except for the heating member 50. FIG. 16 shows the heating member 50 in the seventh embodiment of this invention. The heating member 50 of FIG. 16 includes three straight line segments composing portions of the electric path between the high-voltage-side lead portion 551 and the low-voltage-side lead portion 552.

Eighth Embodiment

Figure 17:
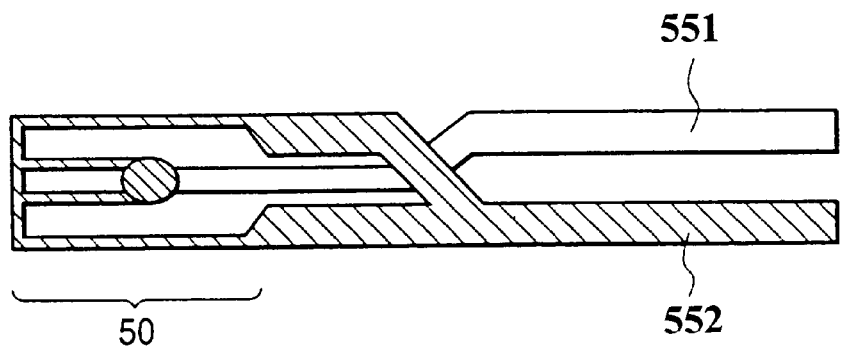
FIG. 17 is a diagram of a heating member, a high-voltage-side lead portion, and a low-voltage-side lead portion in a gas sensor according to an eighth embodiment of this invention.

An eighth embodiment of this invention is similar to the first embodiment thereof except for the heating member 50. FIG. 17 shows the heating member 50 in the eighth embodiment of this invention. The heating member 50 of FIG. 17 includes four straight line segments composing portions of the electric path between the high-voltage-side lead portion 551 and the low-voltage-side lead portion 552.

Ninth Embodiment

Figure 18:
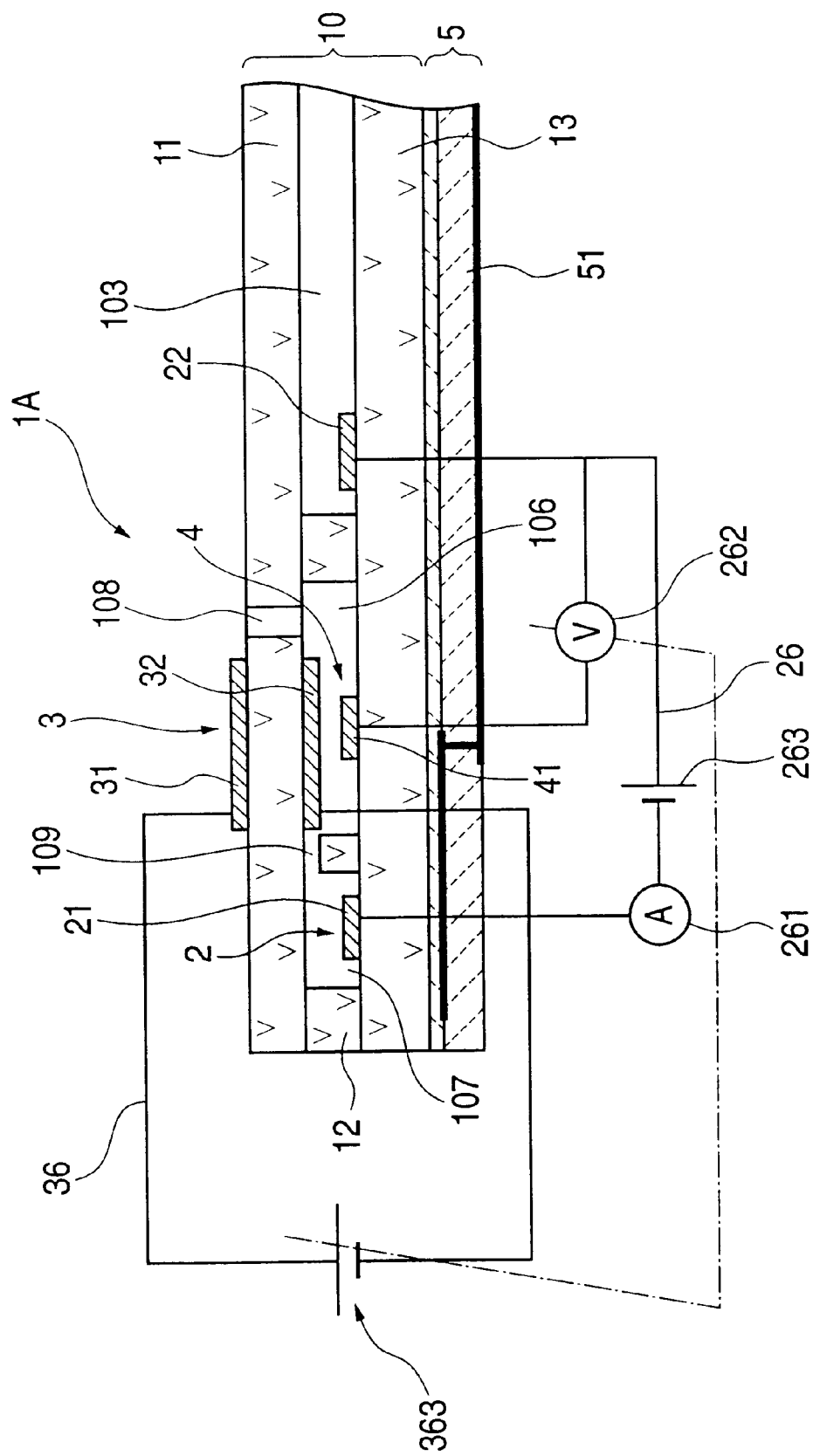
FIG. 18 is a sectional diagram of a gas sensor according to a ninth embodiment of this invention.

FIG. 18 shows a gas sensor 1A according to a ninth embodiment of this invention. The gas sensor 1A in the ninth embodiment of this invention is similar to that in one of the first to eighth embodiments thereof except for design changes indicated below.

As shown in FIG. 18, the gas sensor 1A has chambers 106 and 107 into which a measurement gas is introduced. Also, the gas sensor 1A has a chamber 103 into which a reference gas is introduced.

The gas sensor 1A has a body 10 including a laminate of solid electrolyte layers 11, 12, and 13. The gas sensor 1A includes a heater portion 5 located below the sensor body 10. The heater portion 5 is similar to that in one of the first to eighth embodiments of this invention. The solid electrolyte layer 12 has openings for forming the first measurement-gas chamber 106, the second measurement-gas chamber 107, and the reference-gas chamber 103. Specifically, the first and second measurement-gas chambers 106 and 107 are defined among the solid electrolyte layers 11, 12, and 13. In addition, the reference-gas chamber 103 is defined among the solid electrolyte layers 11, 12, and 13. The solid electrode layer 13 extends on the heater portion 5.

The first measurement-gas chamber 106 communicates with an external space around the gas sensor 1A via a first diffusion controlling passage 108 in the solid electrolyte layer 11. The measurement gas is introduced from the external space into the first measurement-gas chamber 106 via the first diffusion controlling passage 108. The first and second measurement-gas chambers 106 and 107 communicate with each other via a second diffusion controlling passage 109. The measurement gas can be introduced from the first measurement-gas chamber 106 into the second measurement-gas chamber 107 via the second diffusion controlling passage 109.

The gas sensor 1A includes a detecting cell 2, a pumping cell 3, and an oxygen sensing cell 4. The detecting cell 2 has a measuring electrode 21, a reference electrode 22, and the solid electrolyte layer 13. The measuring electrode 21 and the reference electrode 22 are provided on the solid electrolyte layer 13. The measuring electrode 21 faces the second measurement-gas chamber 107. The reference electrode 22 faces the reference-gas chamber 103. The measuring electrode 22 is made of platinum (Pt) which is active to NOx, that is, which decomposes NOx.

The pumping cell 3 has the solid electrolyte layer 11, and a pair of pumping electrodes 31 and 32 formed on the opposite sides of the solid electrolyte layer 11 respectively. The pumping electrodes 31 and 32 are parallel and align with each other. The pumping electrode 31 is exposed at an exterior of the gas sensor 1A. The pumping electrode 32 faces the first measurement-gas chamber 106. The pumping electrode 32 is made of a gold-platinum alloy (Au—Pt) which is inactive to NOx, that is, which does not decompose NOx.

The oxygen sensing cell 4 has the solid electrolyte layer 13, a measuring electrode 41, and the reference electrode 22. The measuring electrode 41 is provided on the solid electrolyte layer 13. The measuring electrode 41 faces the first measurement-gas chamber 106. The measuring electrode 41 is made of a gold-platinum alloy (Au—Pt) which is inactive to NOx, that is, which does not decompose NOx.

An electric circuit 26 is connected to the detecting cell 2 and the oxygen sensing cell 4. The electric circuit 26 includes a current meter 261, a voltage meter 263, and a constant-voltage power supply 263. The positive terminal of the power supply 263 is electrically connected to the reference electrode 22. The negative terminal of the power supply 263 is electrically connected via the current meter 261 to the measuring electrode 21. The voltage meter 262 is electrically connected between the measuring electrode 41 and the reference electrode 22.

An electric circuit 36 is connected to the pumping cell 3. The electric circuit 36 includes a variable-voltage power supply 363. The positive terminal of the power supply 363 is electrically connected to the electrode 31 of the pumping cell 3. The negative terminal of the power supply 363 is electrically connected to the electrode 32 of the pumping cell 3. The power supply 363 is connected to the voltage meter 262. The output voltage of the power supply 363 varies in response to the detected voltage value provided by the voltage meter 262.

The gas sensor 1A operates as follows. A measurement gas (for example, an engine exhaust gas) is introduced into the first measurement-gas chamber 106 via the first diffusion controlling passage 108. The measurement gas is introduced from the first measurement-gas chamber 106 to the second measurement-gas chamber 107 via the second diffusion controlling passage 109. A reference gas (for example, an atmosphere) is introduced into the reference-gas chamber 103.

The voltage generated by the power supply 363 is applied to the pumping cell 3. The voltage application activates the pumping cell 3. Since the electrode 32 of the pumping cell 3 is inactive to NOx, only oxygen ($O_2$) is pumped from the measurement gas in the first measurement-gas chamber 106 via the pumping cell 3. Specifically, the oxygen ($O_2$) is drawn into the pumping cell 3 from the first measurement-gas chamber 106, being transferred through the pumping cell 3 before being discharged via the pumping electrode 31 into the external space.

In the oxygen sensing cell 4, an electromotive force is induced between the measuring electrode 41 and the reference electrode 22. This electromotive force depends on a difference in oxygen concentration between the measurement gas in the first measurement-gas chamber 106 and the reference gas in the reference-gas chamber 103. The electromotive force is measured by the voltage meter 262 as an indication of the oxygen partial pressure in the measurement gas within the first measurement-gas chamber 106. The voltage generated by the power supply 363, that is, the voltage applied to the pumping cell 3, varies in response to the measured electromotive-force value provided by the voltage meter 262. The relation between the applied voltage and the measured electromotive-force value is designed to maintain the oxygen partial pressure in the measurement gas within the first measurement-gas chamber 106 at a desired constant level.

The pumping cell 3 separates only a portion of the oxygen ($O_2$) component from the measurement gas in the first measurement-gas chamber 106. Therefore, the measurement gas which contains a remaining portion of the oxygen ($O_2$) component flows from the first measurement-gas chamber 106 into the second measurement-gas chamber 107. The voltage generated by the power supply 263 is applied to the detecting cell 2. The voltage application activates the detecting cell 2. The measuring electrode 21 of the detecting cell 2 decomposes NOx in the surrounding measurement gas within the second measurement-gas chamber 107 through a reaction as "NOx→$(1/2)N_2$+ $(x/2)O_2$". Thus, the decomposition of NOx causes new oxygen ($O_2$). The remaining oxygen ($O_2$) and the new oxygen ($O_2$) are drawn into the detecting cell 2 from the second measurement-gas chamber 107, being transferred through the detecting cell 2 before being discharged via the reference electrode 22 into the reference-gas chamber 103. At this time, an electric current which flows through the detecting cell 2 is detected by the current meter 261 as an indication of the NOx-gas concentration in the measurement gas. The remaining oxygen ($O_2$) causes a decomposition current which is an offset current superimposed on the NOx-concentration-indicating electric current flowing through the detecting cell 2.

What is claimed is:

1. A gas sensor comprising:

a body having a measurement-gas chamber and a reference-gas chamber, the measurement-gas chamber being supplied with a measurement gas, the reference-gas chamber being supplied with a reference gas;

a detecting cell provided in the body and including (1) a solid electrolyte member, (2) a measuring electrode provided on the solid electrolyte member and facing the measurement-gas chamber and (3) a reference electrode provided on the solid electrolyte member and facing the reference-gas chamber; and a heater portion for heating the detecting cell, the heater portion including (1) a substrate, (2) a heating member provided on the substrate, and (3) a high-voltage-side lead portion provided on the substrate and electrically connected to the heating member;

wherein the substrate has a first surface and a second surface opposite to each other, and the first surface of the substrate faces the body, and wherein the heating member extends on the first surface of the substrate, and the high-voltage-side lead portion extends on the second surface of the substrate; and wherein approximately the entirety of the length of the high-voltage-side lead portion is disposed on the second surface of the substrate such that leakage current from the high-voltage-side lead portion is substantially prevented from affecting the output of the sensor.

2. A gas sensor as recited in claim 1, wherein the heater portion further includes a low-voltage-side lead portion provided on the substrate and electrically connected to the heating member, the low-voltage-side lead portion extending on the first surface of the substrate.

3. A gas sensor as recited in claim 2, wherein the heater portion further includes an insulating member provided on the substrate and having an opening of a negative pattern with respect to the heating member and the low-voltage-side lead portion, and wherein the heating member and the low-voltage-side lead portion fit in the opening in the insulating member.

4. A gas sensor comprising:

a body having a measurement-gas chamber and a reference-gas chamber, the measurement-gas chamber being supplied with a measurement gas, the reference-gas chamber being supplied with a reference gas;

a detecting cell provided in the body and including (1) a solid electrolyte member, (2) a measuring electrode provided on the solid electrolyte member and facing the measurement-gas chamber, and (3) a reference electrode provided on the solid electrolyte member and facing the reference-gas chamber, a heater portion for heating the detecting cell, the heater portion including (1) a first substrate, (2) a heating member provided on the first substrate, (3) a high-voltage-side lead portion provided on the first substrate and electrically connected to the heating member, (4) a low-voltage-side lead portion provided on the first substrate and electrically connected to the heating member, and (5) a second substrate covering the heating member;

wherein the first substrate has a first surface and a second surface opposite to each other, and the first surface of the first substrate faces the body, and wherein the heating member extends on the first surface of the first substrate, and the high-voltage-side lead portion extends on the second surface of the first substrate; and wherein approximately the entirety of the length of the high-voltage-side lead portion is disposed on the second surface of the substrate such that leakage current from the high-voltage-side lead portion is substantially prevented from affecting the output of the sensor.

5. A gas sensor comprising:

a body having a measurement-gas chamber and a reference-gas chamber, the measurement-gas chamber being supplied with a measurement gas, the reference-gas chamber being supplied with a reference gas;

a detecting cell provided in the body and including (1) a solid electrolyte member, (2) a measuring electrode provided on the solid electrolyte member and facing the measurement-gas chamber, and (3) a reference electrode provided on the solid electrolyte member and facing the reference-gas chamber; and a heater portion for heating the detecting cell, the heater portion including (1) a substrate, (2) a heating member provided on the substrate, and (3) a high-voltage-side lead portion provided on the substrate and electrically and directly connected to the heating member without any other lead portion disposed on the same surface of the substrate as the heater member and connected therebetween;

wherein the substrate has a first surface and a second surface opposite to each other, and the first surface of the substrate faces the body, and wherein the heating member extends on the first surface of the substrate, and the high-voltage-side lead portion extends on the second surface of the substrate.

6. A gas sensor as recited in claim 5, wherein the substrate has a through hole via which the high-voltage-side lead portion is electrically and directly connected to the heating member.

7. A gas sensor as recited in claim 5, wherein the heating member includes a low-voltage-side portion and a high-voltage-side portion, and the high-voltage-side portion is surrounded by the low-voltage-side portion.

8. A gas sensor comprising:

a body having a measurement-gas chamber and a reference-gas chamber, the measurement-gas chamber being supplied with a measurement gas, the reference-gas chamber being supplied with a reference gas;

a detecting cell provided in the body and including (1) a solid electrolyte member, (2) a measuring electrode provided on the solid electrolyte member and facing the measurement-gas chamber, and (3) a reference electrode provided on the solid electrolyte member and facing the reference-gas chamber; and a heater portion for heating the detecting cell, the heater portion including (1) a substrate, (2) a heating member provided on the substrate, (3) a high-voltage-side lead portion provided on the substrate and electrically connected to the heating member; and (4) a low-voltage-side lead portion provided on the substrate and electrically connected to the heating member;

wherein the substrate has a first surface and a second surface opposite to each other, and the first surface of the substrate faces the body, wherein the heating member and the low-voltage-side lead portion extend on the first surface of the substrate, and the heater portion further includes an insulating member provided on the substrate and having a pre-formed opening of a negative pattern with respect to the heating member and the low-voltage-side lead portion, and wherein the heating member and the low-voltage-side lead portion fit in the pre-formed opening in the insulating member.

* * * * *